(12) United States Patent
Cao et al.

(10) Patent No.: US 10,539,691 B2
(45) Date of Patent: Jan. 21, 2020

(54) DETECTOR FOR X-RAY FLUORESCENCE

(71) Applicant: SHENZHEN XPECTVISION TECHNOLOGY CO., LTD., Shenzhen (CN)

(72) Inventors: Peiyan Cao, Shenzhen (CN); Yurun Liu, Shenzhen (CN)

(73) Assignee: SHENZHEN XPECTVISION TECHNOLOGY CO., LTD., Shenzhen (CN)

( * ) Notice: Subject to any disclaimer, the term of this patent is extended or adjusted under 35 U.S.C. 154(b) by 15 days.

(21) Appl. No.: 15/309,036

(22) PCT Filed: Jun. 10, 2015

(86) PCT No.: PCT/CN2015/081126
§ 371 (c)(1),
(2) Date: Nov. 4, 2016

(87) PCT Pub. No.: WO2016/197338
PCT Pub. Date: Dec. 15, 2016

(65) Prior Publication Data
US 2018/0081071 A1     Mar. 22, 2018

(51) Int. Cl.
*G01T 1/24* (2006.01)
*H01L 27/146* (2006.01)

(52) U.S. Cl.
CPC ........ *G01T 1/247* (2013.01); *H01L 27/14636* (2013.01); *H01L 27/14659* (2013.01); *H01L 27/14661* (2013.01); *G01N 2223/076* (2013.01)

(58) Field of Classification Search
CPC ........ G01N 2223/076; G01N 2223/501; G01T 1/247; G01T 1/366; H01L 27/14636; H01L 27/14659; H01L 27/14661
See application file for complete search history.

(56) References Cited

U.S. PATENT DOCUMENTS

| 5,245,191 A | 9/1993 | Barber et al. |
| 5,389,792 A | 2/1995 | DiMarzio et al. |
| 2002/0117627 A1* | 8/2002 | Jimbo ............... G01T 1/161 250/370.13 |

(Continued)

FOREIGN PATENT DOCUMENTS

| CN | 1675780 A | 9/2005 |
| CN | 1892250 A | 1/2007 |

(Continued)

*Primary Examiner* — Chih-Cheng Kao
(74) *Attorney, Agent, or Firm* — IPro, PLLC; Qian Gu (57) ABSTRACT

Disclosed herein is a detector, comprising: a plurality of pixels, each pixel configured to count numbers of X-ray photons incident thereon whose energy falls in a plurality of bins, within a period of time; and wherein the detector is configured to add the numbers of X-ray photons for the bins of the same energy range counted by all the pixels. Each of the pixels may comprise an analog-to-digital converter (ADC) configured to digitize an analog signal representing the energy of an incident X-ray photon into a digital signal. The pixels may be able to operate in parallel. Each of the pixels may be able to measure its dark current, such as before or concurrently with each X-ray photon incident thereon.

22 Claims, 12 Drawing Sheets

(56) References Cited

U.S. PATENT DOCUMENTS

| | | | | |
|---|---|---|---|---|
| 2003/0122084 | A1* | 7/2003 | Desaute | G01T 1/17 250/395 |
| 2004/0232949 | A1* | 11/2004 | Arques | G01T 1/171 327/103 |
| 2006/0050160 | A1 | 3/2006 | Suzuki et al. | |
| 2009/0039273 | A1 | 2/2009 | Tkaczyk et al. | |
| 2009/0046913 | A1* | 2/2009 | Chandra | A61B 6/035 382/131 |
| 2010/0020924 | A1* | 1/2010 | Steadman Booker | G01T 1/17 378/19 |
| 2010/0181491 | A1 | 7/2010 | Karim et al. | |
| 2010/0225837 | A1 | 9/2010 | Seki et al. | |
| 2011/0064293 | A1* | 3/2011 | Takayama | A61B 6/037 250/370.08 |
| 2012/0105262 | A1* | 5/2012 | Rao | H03M 1/123 341/155 |
| 2013/0028382 | A1 | 1/2013 | Spahn | |
| 2013/0284940 | A1* | 10/2013 | Herrmann | G01T 1/17 250/393 |
| 2014/0016748 | A1* | 1/2014 | Spahn | G01T 1/247 378/62 |
| 2014/0110595 | A1 | 4/2014 | Iwakiri et al. | |
| 2014/0328464 | A1* | 11/2014 | Proksa | G01N 23/046 378/62 |
| 2014/0334600 | A1 | 11/2014 | Lee et al. | |

FOREIGN PATENT DOCUMENTS

| | | |
|---|---|---|
| CN | 1947660 A | 4/2007 |
| CN | 101389978 A | 3/2009 |
| CN | 101558325 A | 10/2009 |
| CN | 101578535 A | 11/2009 |
| CN | 101600974 A | 12/2009 |
| CN | 101644780 A | 2/2010 |
| CN | 101862200 A | 10/2010 |
| CN | 101903802 A | 12/2010 |
| CN | 102016637 A | 4/2011 |
| CN | 102124372 A | 7/2011 |
| CN | 101297221 B | 1/2012 |
| CN | 102655159 A | 9/2012 |
| CN | 102805628 A | 12/2012 |
| CN | 103109205 A | 5/2013 |
| CN | 103296035 A | 9/2013 |
| CN | 101578535 B | 11/2013 |
| CN | 103430533 A | 12/2013 |
| CN | 103576179 A | 2/2014 |
| CN | 103592673 A | 2/2014 |
| CN | 103633187 A | 3/2014 |
| CN | 103715214 A | 4/2014 |
| CN | 103975580 A | 8/2014 |
| CN | 104434152 A | 3/2015 |
| CN | 107533146 A | 1/2018 |
| CN | 103975580 B | 10/2018 |
| DE | 102012215818 A1 | 3/2014 |
| JP | 2002217444 A | 8/2002 |
| JP | 2004362905 A | 12/2004 |
| JP | 4734224 B2 | 7/2011 |
| JP | 2013142578 A | 7/2013 |
| KR | 101410736 B1 | 6/2014 |
| WO | WO-02103391 A1 | 12/2002 |
| WO | 2008072181 A2 | 6/2008 |
| WO | 2012095710 A2 | 7/2012 |
| WO | WO-2013012809 A1 | 1/2013 |
| WO | 2016161542 A1 | 10/2016 |

\* cited by examiner

DETECTOR FOR X-RAY FLUORESCENCE

TECHNICAL FIELD

The disclosure herein relates to a detector suitable for X-ray fluorescence.

BACKGROUND

X-ray fluorescence (XRF) is the emission of characteristic fluorescent X-rays from a material that has been excited by, for example, exposure to high-energy X-rays or gamma rays. An electron on an inner orbital of an atom may be ejected, leaving a vacancy on the inner orbital, if the atom is exposed to X-rays or gamma rays with photon energy greater than the ionization potential of the electron. When an electron on an outer orbital of the atom relaxes to fill the vacancy on the inner orbital, an X-ray (fluorescent X-ray or secondary X-ray) is emitted. The emitted X-ray has a photon energy equal the energy difference between the outer orbital and inner orbital electrons.

Figure 1A:
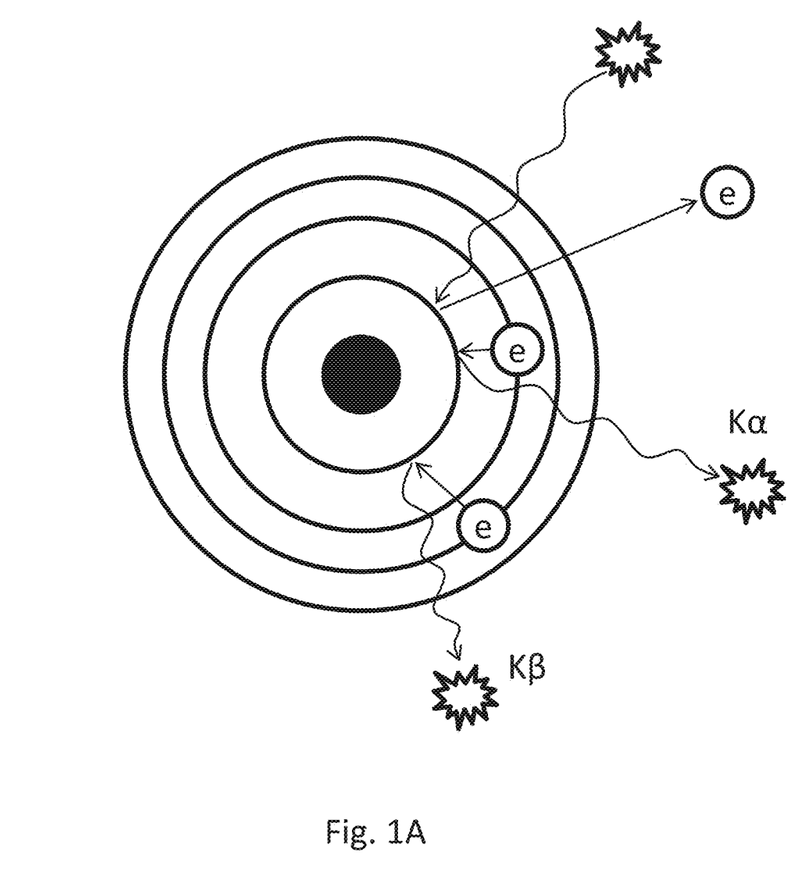
FIG. 1A and FIG. 1B schematically show mechanisms of XRF.
Figure 1B:
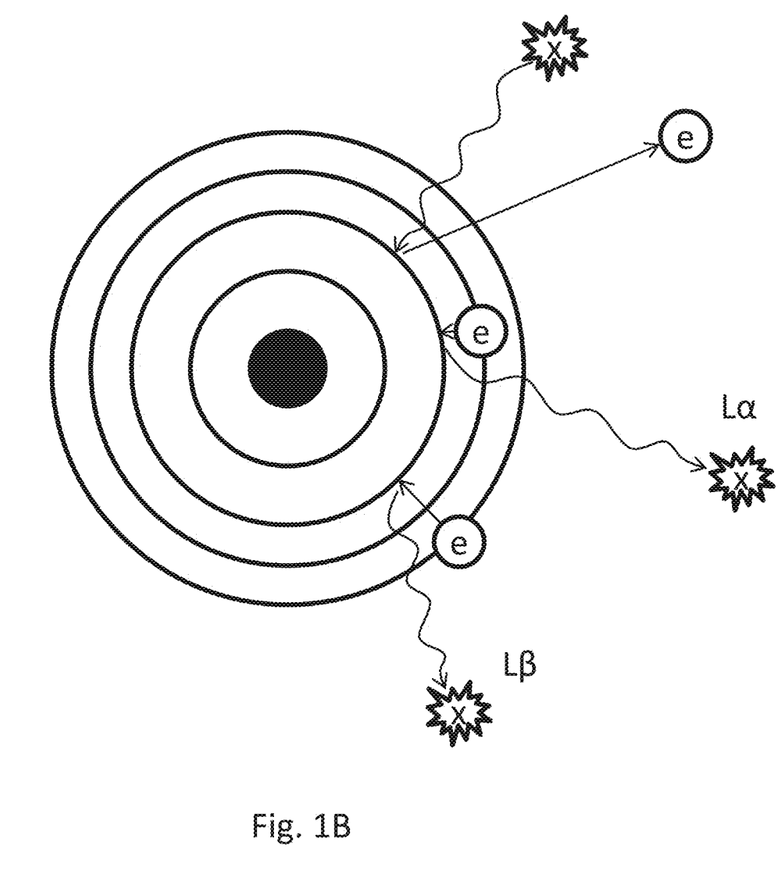

For a given atom, the number of possible relaxations is limited. As shown in FIG. 1A, when an electron on the L orbital relaxes to fill a vacancy on the K orbital (L→K), the fluorescent X-ray is called Kα. The fluorescent X-ray from M→K relaxation is called Kβ. As shown in FIG. 1B, the fluorescent X-ray from M→L relaxation is called Lα, and so on.

Analyzing the fluorescent X-ray spectrum can identify the elements in a sample because each element has orbitals of characteristic energy. The fluorescent X-ray can be analyzed either by sorting the energies of the photons (energy-dispersive analysis) or by separating the wavelengths of the fluorescent X-ray (wavelength-dispersive analysis). The intensity of each characteristic energy peak is directly related to the amount of each element in the sample.

Proportional counters or various types of solid-state detectors (PIN diode, Si(Li), Ge(Li), Silicon Drift Detector SDD) may be used in energy dispersive analysis. These detectors are based on the same principle: an incoming X-ray photon ionizes a large number of detector atoms with the amount of charge carriers produced being proportional to the energy of the incoming X-ray photon. The charge carriers are collected and counted to determine the energy of the incoming X-ray photon and the process repeats itself for the next incoming X-ray photon. After detection of many X-ray photons, a spectrum may be compiled by counting the number of X-ray photons as a function of their energy. The speed of these detectors is limited because the charge carriers generated by one incoming X-ray photon must be collected before the next incoming X-ray hits the detector.

Wavelength dispersive analysis typically uses a photomultiplier. The X-ray photons of a single wavelength are selected from the incoming X-ray a monochromator and are passed into the photomultiplier. The photomultiplier counts individual X-ray photons as they pass through. The counter is a chamber containing a gas that is ionizable by X-ray photons. A central electrode is charged at (typically)+1700 V with respect to the conducting chamber walls, and each X-ray photon triggers a pulse-like cascade of current across this field. The signal is amplified and transformed into an accumulating digital count. These counts are used to determine the intensity of the X-ray at the single wavelength selected.

SUMMARY

Disclosed herein is a detector, comprising: a plurality of pixels, each pixel configured to count numbers of X-ray photons incident thereon whose energy falls in a plurality of bins, within a period of time; and wherein the detector is configured to add the numbers of X-ray photons for the bins of the same energy range counted by all the pixels.

According to an embodiment, the detector is further configured to compile the added numbers as a spectrum of the X-ray photons incident on the detector.

According to an embodiment, the plurality of pixels area arranged in an array.

According to an embodiment, the pixels are configured to count the numbers of X-ray photons within a same period of time.

According to an embodiment, each of the pixels comprises an analog-to-digital converter (ADC) configured to digitize an analog signal representing the energy of an incident X-ray photon into a digital signal.

According to an embodiment, the pixels are configured to operate in parallel.

According to an embodiment, each of the pixels is configured to measure its dark current.

According to an embodiment, each of the pixels is configured to measure its dark current before or concurrently with each X-ray photon incident thereon.

According to an embodiment, each of the pixels is configured to deduct a contribution of the dark current from the energy of an X-ray photon incident thereon.

According to an embodiment, each of the pixels is configured to measure its dark current by measuring a time it takes for a voltage to increase by a threshold.

According to an embodiment, the ADC is a successive-approximation-register (SAR) ADC.

According to an embodiment, the detector further comprises: an X-ray absorption layer comprising an electric contact; a first voltage comparator configured to compare a voltage of the electric contact to a first threshold; a second voltage comparator configured to compare the voltage to a second threshold; a controller; a plurality of counters each associated with a bin and configured to register a number of X-ray photons absorbed by one of the pixels wherein the energy of the X-ray photons falls in the bin; wherein the controller is configured to start a time delay from a time at which the first voltage comparator determines that an absolute value of the voltage equals or exceeds an absolute value of the first threshold; wherein the controller is configured to determine whether an energy of an X-ray photon falls into the bin; wherein the controller is configured to cause the number registered by the counter associated with the bin to increase by one.

According to an embodiment, the detector further comprises a capacitor module electrically connected to the electric contact, wherein the capacitor module is configured to collect charge carriers from the electric contact.

According to an embodiment, the controller is configured to activate the second voltage comparator at a beginning or expiration of the time delay.

According to an embodiment, the controller is configured to connect the electric contact to an electrical ground.

According to an embodiment, a rate of change of the voltage is substantially zero at expiration of the time delay.

According to an embodiment, the X-ray absorption layer comprises a diode.

The detector of claim 12, wherein the X-ray absorption layer comprises silicon, germanium, GaAs, CdTe, CdZnTe, or a combination thereof.

According to an embodiment, the apparatus does not comprise a scintillator.

Disclosed herein is a method for measuring an energy spectrum of X-ray, comprising: exposing a detector with a plurality of pixels to X-ray; determining a number of X-ray photons for each pixel for one of a plurality of bins, wherein energy of the X-ray photon falls in the one bin; adding the numbers for the bins of a same energy range of all the pixels.

According to an embodiment, determining the number comprises subtracting a contribution of dark current in the each pixel.

According to an embodiment, determining the number comprises analog-to-digital conversion.

DETAILED DESCRIPTION

Figure 2:
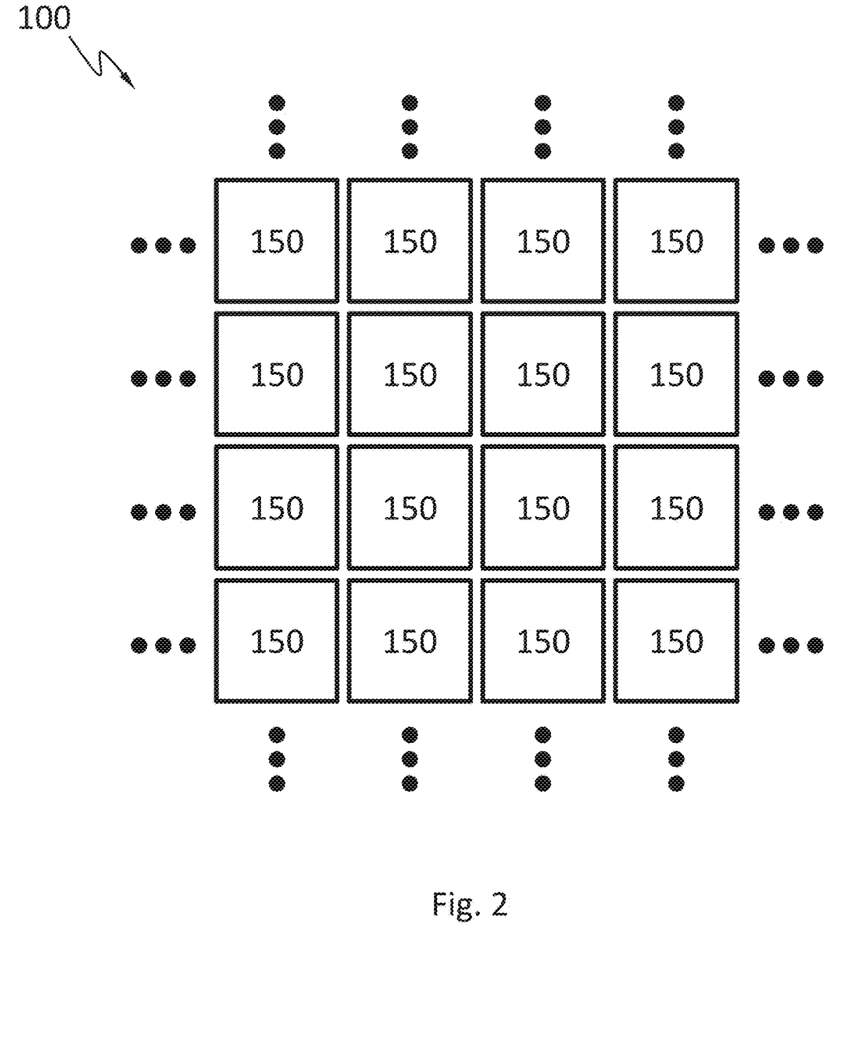
FIG. 2 schematically shows a detector suitable for XRF, according to an embodiment.

FIG. 2 schematically shows a detector 100 suitable for XRF, according to an embodiment. The detector has an array of pixels 150. The array may be a rectangular array, a honeycomb array, a hexagonal array or any other suitable array. Each pixel 150 is configured to detect an X-ray photon incident thereon and measure the energy of the X-ray photon. For example, each pixel 150 is configured to count numbers of X-ray photons incident thereon whose energy falls in a plurality of bins, within a period of time. All the pixels 150 may be configured to count the numbers of X-ray photons incident thereon within a plurality of bins of energy within the same period of time. Each pixel 150 may have its own analog-to-digital converter (ADC) configured to digitize an analog signal representing the energy of an incident X-ray photon into a digital signal. For XRF applications, an ADC with a 10-bit resolution or higher is useful. Each pixel 150 may be configured to measure its dark current, such as before or concurrently with each X-ray photon incident thereon. Each pixel 150 may be configured to deduct the contribution of the dark current from the energy of the X-ray photon incident thereon. The pixels 150 may be configured to operate in parallel. For example, when one pixel 150 measures an incident X-ray photon, another pixel 150 may be waiting for an X-ray photon to arrive. The pixels 150 may not have to be individually addressable.

The detector 100 may have at least 100, 2500, 10000, or more pixels 150. The detector 100 may be configured to add the numbers of X-ray photons for the bins of the same energy range counted by all the pixels 150. For example, the detector 100 may add the numbers the pixels 150 stored in a bin for energy from 70 KeV to 71 KeV, add the numbers the pixels 150 stored in a bin for energy from 71 KeV to 72 KeV, and so on. The detector 100 may compile the added numbers for the bins as a spectrum of the X-ray photons incident on the detector 100.

Figure 3:
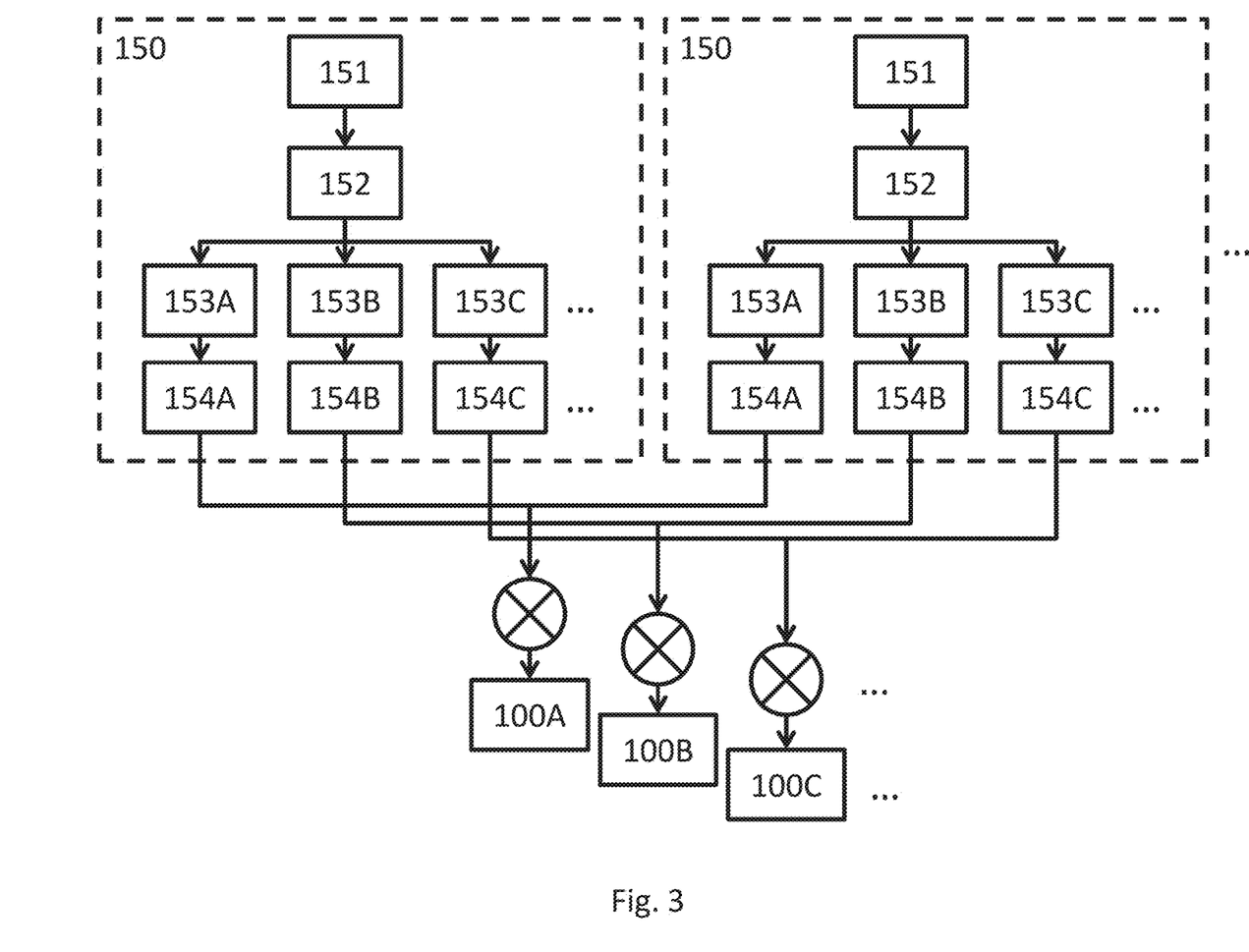
FIG. 3 schematically shows a block diagram for the detector, according to an embodiment.

FIG. 3 schematically shows a block diagram for the detector 100, according to an embodiment. Each pixel 150 may measure the energy 151 of an X-ray photon incident thereon. The energy 151 of the X-ray photon is digitized (e.g., by an ADC) in step 152 into one of a plurality of bins 153A, 153C, 153C . . . . The bins 153A, 153C, 153C . . . each have a corresponding counter 154A, 154B and 154C, respectively. When the energy 151 is allocated into a bin, the number stored in the corresponding counter increases by one. The detector 100 may added the numbers stored in all the counters corresponding to bins for the same energy range in the pixels 150. For example, the numbers stored in all the counters 154C in all pixels 150 may be added and stored in a global counter 100C for the same energy range. The numbers stored in all the global counters may be compiled into an energy spectrum of the X-ray incident on the detector 100.

Figure 4A:
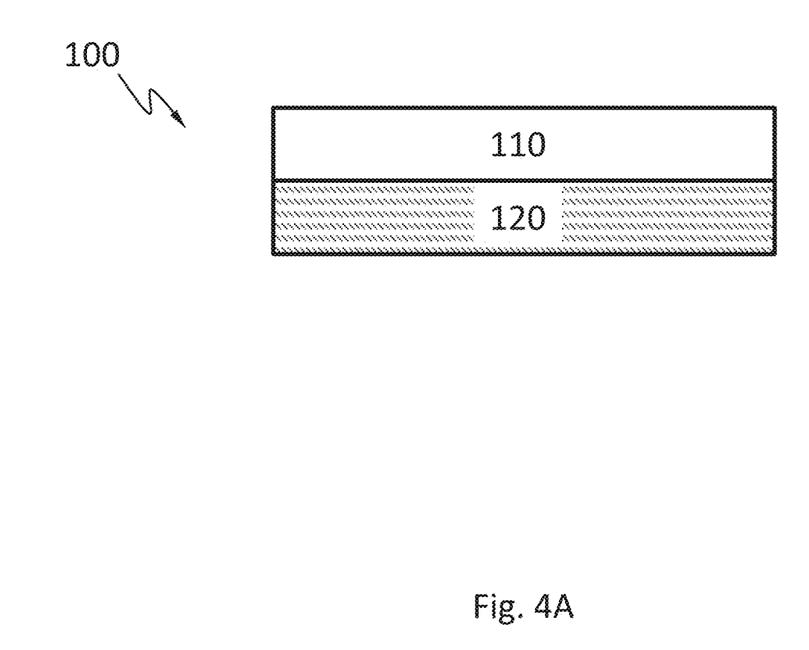
FIG. 4A schematically shows a cross-sectional view of the detector, according to an embodiment.

FIG. 4A schematically shows a cross-sectional view of the detector 100, according to an embodiment. The detector 100 may include an X-ray absorption layer 110 and an electronics layer 120 (e.g., an ASIC) for processing or analyzing electrical signals incident X-ray generates in the X-ray absorption layer 110. In an embodiment, the detector 100 does not comprise a scintillator. The X-ray absorption layer 110 may include a semiconductor material such as, silicon, germanium, GaAs, CdTe, CdZnTe, or a combination thereof. The semiconductor may have a high mass attenuation coefficient for the X-ray energy of interest.

Figure 4B:
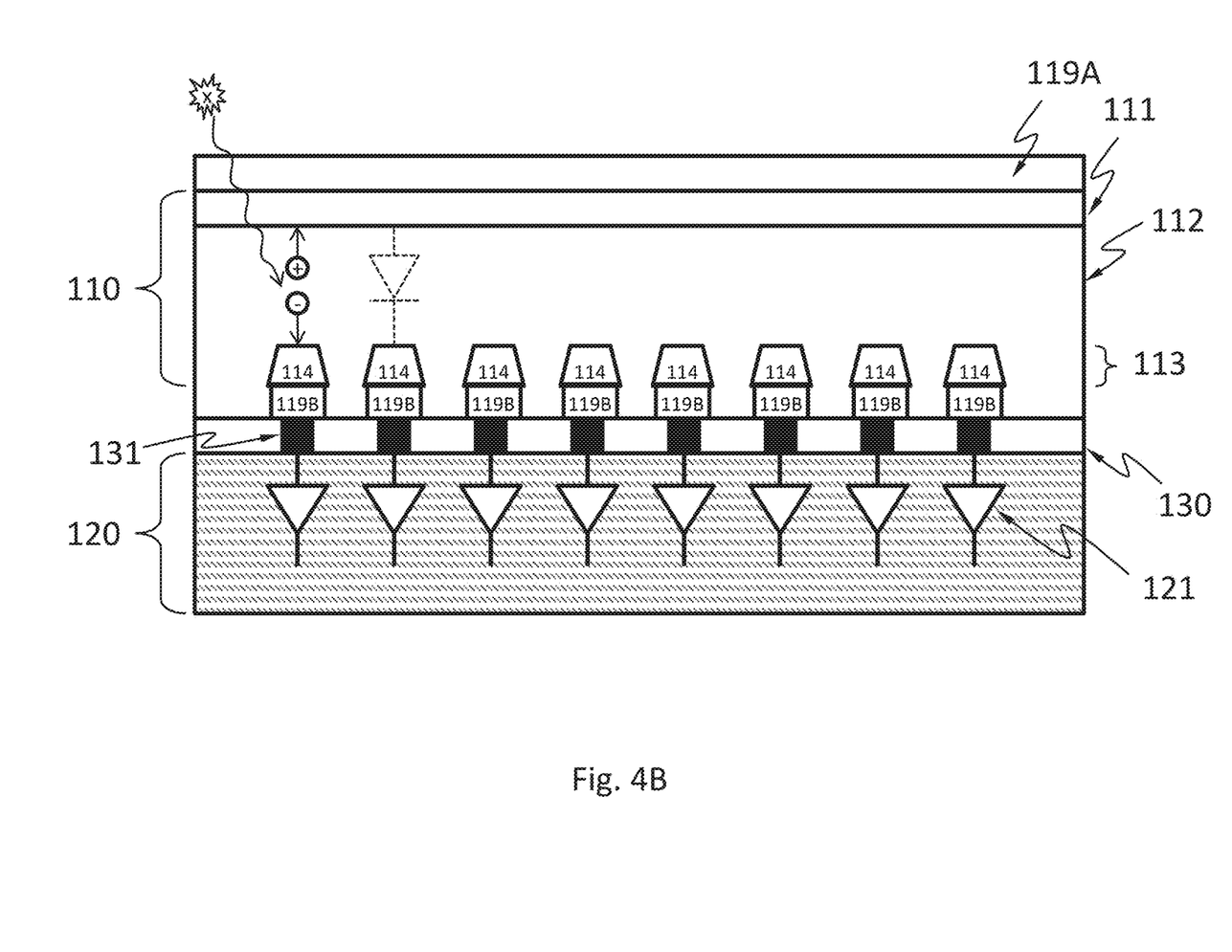
FIG. 4B schematically shows a detailed cross-sectional view of the detector, according to an embodiment.

As shown in a detailed cross-sectional view of the detector 100 in FIG. 4B, according to an embodiment, the X-ray absorption layer 110 may include one or more diodes (e.g., p-i-n or p-n) formed by a first doped region 111, one or more discrete regions 114 of a second doped region 113. The second doped region 113 may be separated from the first doped region 111 by an optional the intrinsic region 112. The discrete portions 114 are separated from one another by the first doped region 111 or the intrinsic region 112. The first doped region 111 and the second doped region 113 have opposite types of doping (e.g., region 111 is p-type and region 113 is n-type, or region 111 is n-type and region 113 is p-type). In the example in FIG. 4B, each of the discrete regions 114 of the second doped region 113 forms a diode with the first doped region 111 and the optional intrinsic region 112. Namely, in the example in FIG. 4B, the X-ray absorption layer 110 has a plurality of diodes having the first doped region 111 as a shared electrode. The first doped region 111 may also have discrete portions.

When an X-ray photon hits the X-ray absorption layer 110 including diodes, the X-ray photon may be absorbed and generate one or more charge carriers by a number of mechanisms. An X-ray photon may generate 10 to 100000 charge carriers. The charge carriers may drift to the electrodes of one of the diodes under an electric field. The field may be an external electric field. The electrical contact 119B may include discrete portions each of which is in electrical contact with the discrete regions 114. In an embodiment, the charge carriers may drift in directions such that the charge carriers generated by a single X-ray photon are not substantially shared by two different discrete regions 114 ("not substantially shared" here means less than 2%, less than 0.5%, less than 0.1%, or less than 0.01% of these charge carriers flow to a different one of the discrete regions 114 than the rest of the charge carriers). Charge carriers generated by an X-ray photon incident around the footprint of one of these discrete regions 114 are not substantially shared with another of these discrete regions 114. A pixel 150 associated with a discrete region 114 may be an area around the discrete region 114 in which substantially all (more than 98%, more than 99.5%, more than 99.9%, or more than 99.99% of) charge carriers generated by an X-ray photon incident therein flow to the discrete region 114. Namely, less than 2%, less than 1%, less than 0.1%, or less than 0.01% of these charge carriers flow beyond the pixel.

Figure 4C:
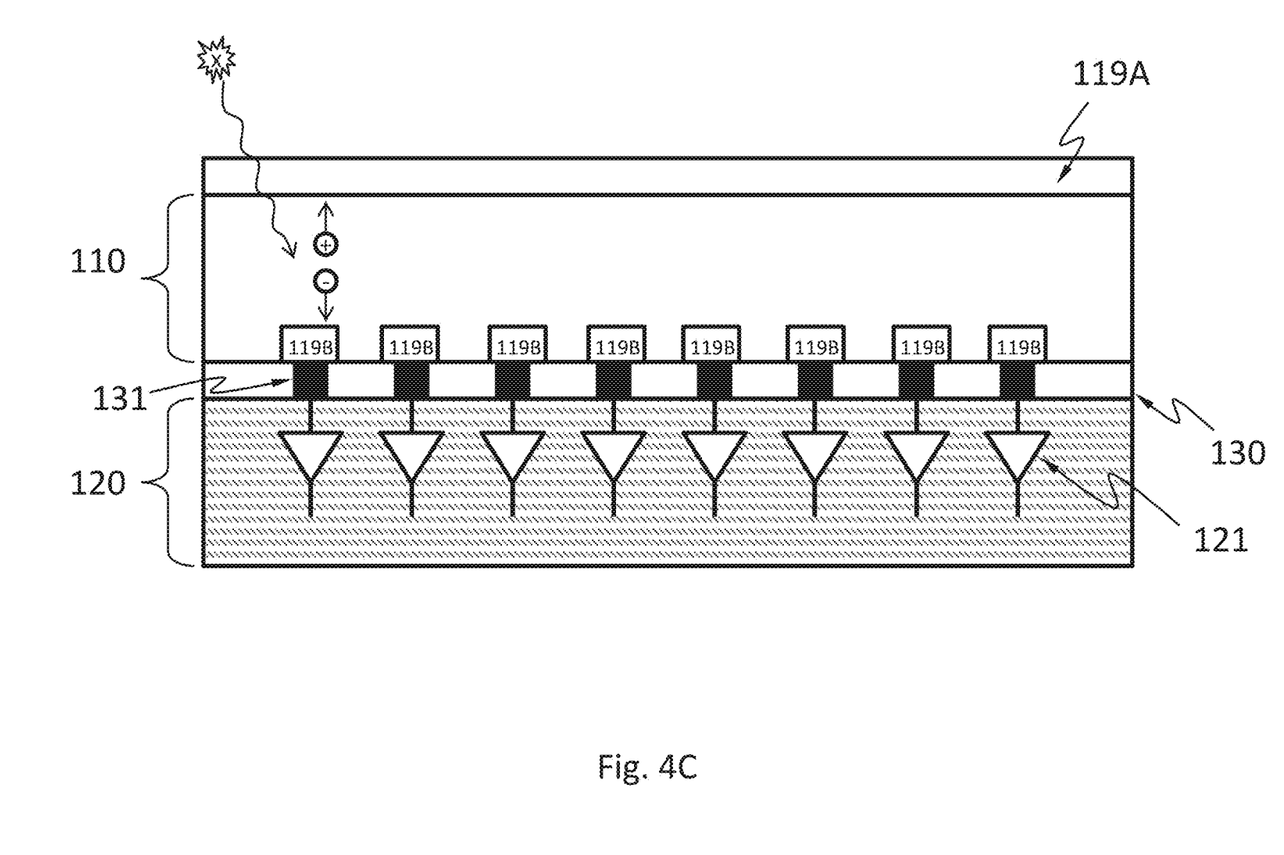
FIG. 4C schematically shows an alternative detailed cross-sectional view of the detector, according to an embodiment.

As shown in an alternative detailed cross-sectional view of the detector 100 in FIG. 4C, according to an embodiment, the X-ray absorption layer 110 may include a resistor of a semiconductor material such as, silicon, germanium, GaAs, CdTe, CdZnTe, or a combination thereof, but does not include a diode. The semiconductor may have a high mass attenuation coefficient for the X-ray energy of interest.

When an X-ray photon hits the X-ray absorption layer 110 including a resistor but not diodes, it may be absorbed and generate one or more charge carriers by a number of mechanisms. An X-ray photon may generate 10 to 100000 charge carriers. The charge carriers may drift to the electrical contacts 119A and 119B under an electric field. The field may be an external electric field. The electrical contact 119B includes discrete portions. In an embodiment, the charge carriers may drift in directions such that the charge carriers generated by a single X-ray photon are not substantially shared by two different discrete portions of the electrical contact 119B ("not substantially shared" here means less than 2%, less than 0.5%, less than 0.1%, or less than 0.01% of these charge carriers flow to a different one of the discrete portions than the rest of the charge carriers). Charge carriers generated by an X-ray photon incident around the footprint of one of these discrete portions of the electrical contact 119B are not substantially shared with another of these discrete portions of the electrical contact 119B. A pixel 150 associated with a discrete portion of the electrical contact 119B may be an area around the discrete portion in which substantially all (more than 98%, more than 99.5%, more than 99.9% or more than 99.99% of) charge carriers generated by an X-ray photon incident therein flow to the discrete portion of the electrical contact 119B. Namely, less than 2%, less than 0.5%, less than 0.1%, or less than 0.01% of these charge carriers flow beyond the pixel associated with the one discrete portion of the electrical contact 119B.

The electronics layer 120 may include an electronic system 121 suitable for processing or interpreting signals generated by X-ray photons incident on the X-ray absorption layer 110. The electronic system 121 may include an analog circuitry such as a filter network, amplifiers, integrators, and comparators, or a digital circuitry such as a microprocessors, and memory. The electronic system 121 may include components shared by the pixels or components dedicated to a single pixel. For example, the electronic system 121 may include an amplifier dedicated to each pixel and a microprocessor shared among all the pixels. The electronic system 121 may be electrically connected to the pixels by vias 131. Space among the vias may be filled with a filler material 130, which may increase the mechanical stability of the connection of the electronics layer 120 to the X-ray absorption layer 110. Other bonding techniques are possible to connect the electronic system 121 to the pixels without using vias.

Figure 5A:
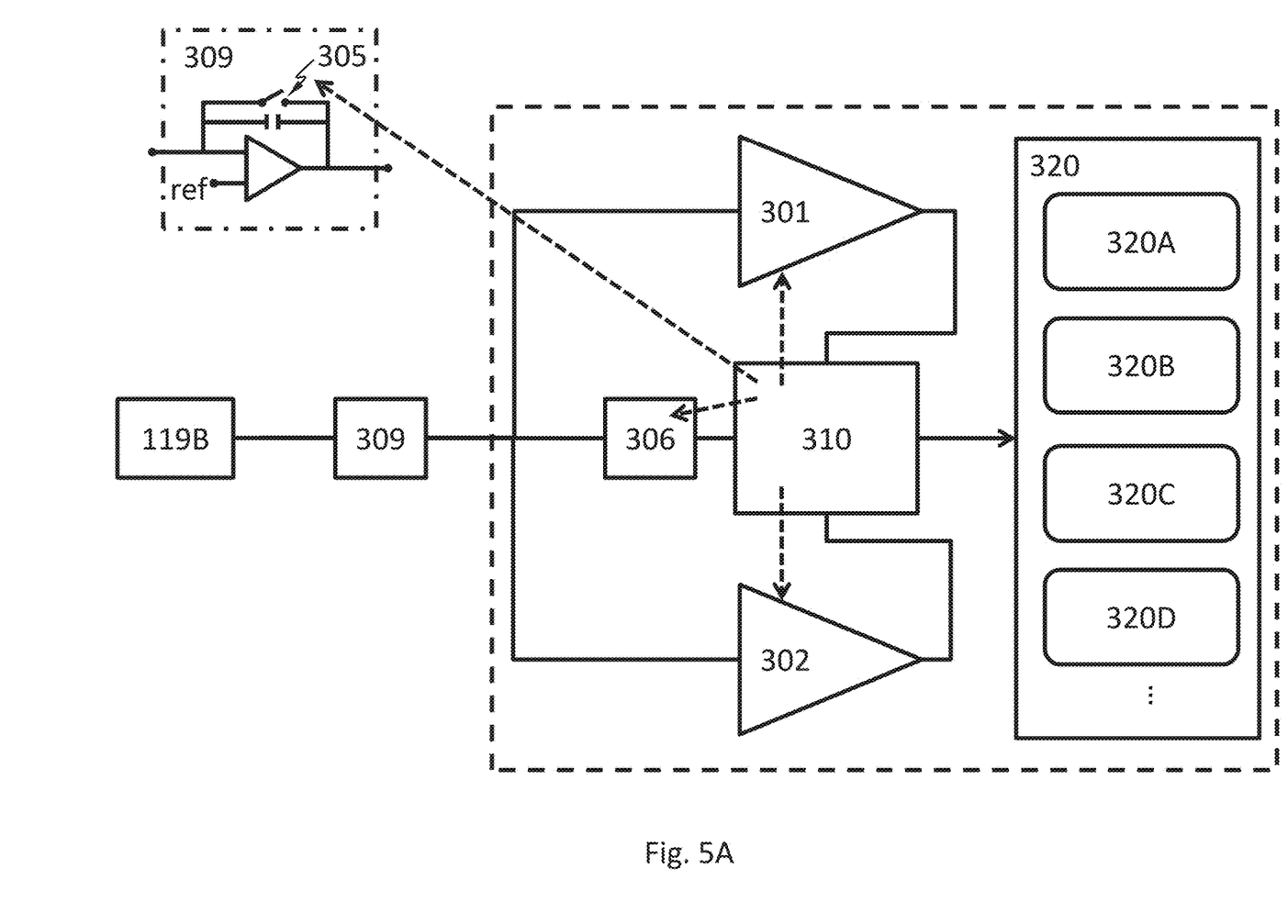
FIG. 5A and FIG. 5B each show a component diagram of the electronic system of the detector, according to an embodiment.
Figure 5B:
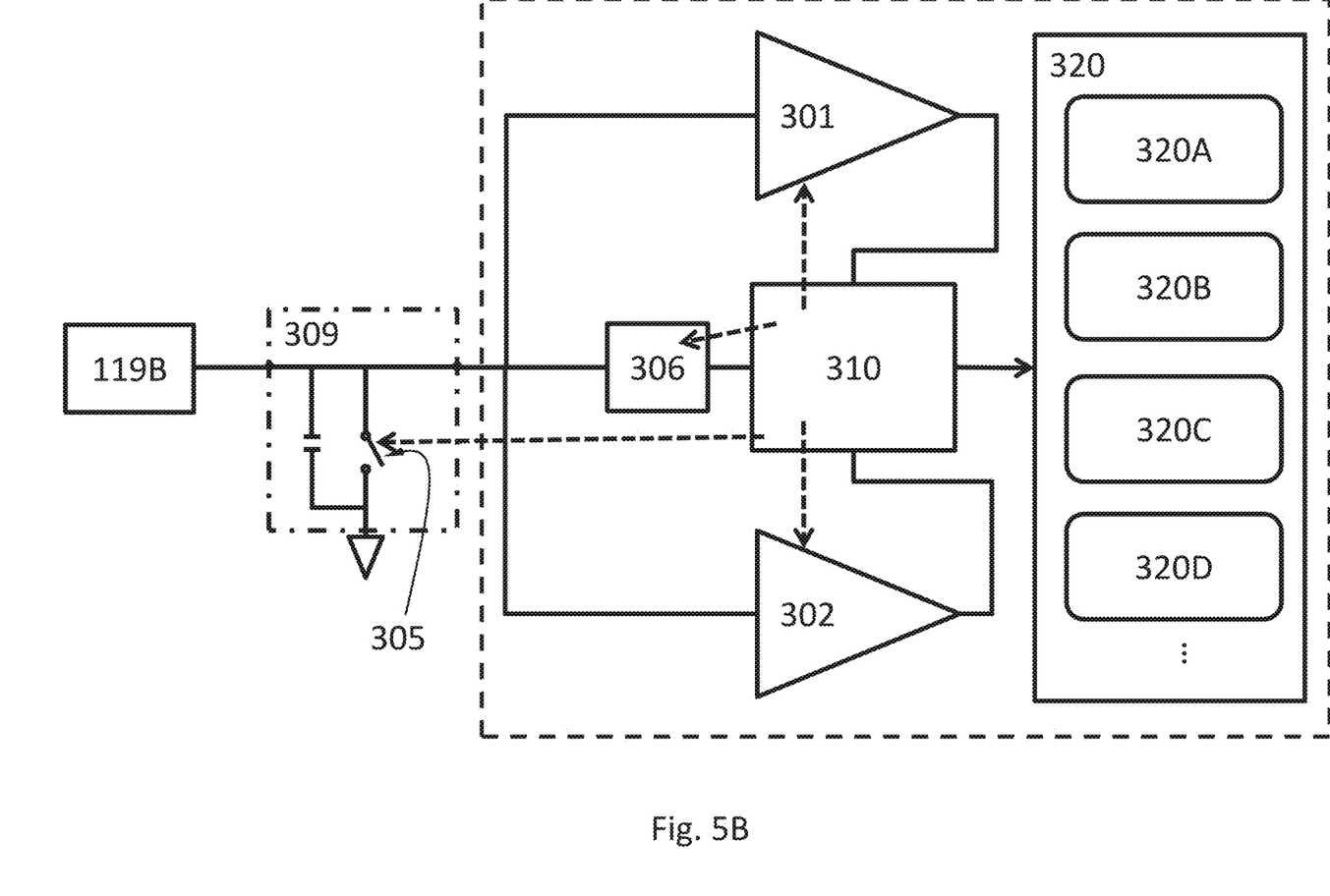

FIG. 5A and FIG. 5B each show a component diagram of the electronic system 121, according to an embodiment. The electronic system 121 may include a first voltage comparator 301, a second voltage comparator 302, a plurality of counters 320 (including counters 320A, 320B, 320C, 320D . . . ), a switch 305, an ADC 306 and a controller 310.

The first voltage comparator 301 is configured to compare the voltage of a discrete portion of the electric contact 119B to a first threshold. The first voltage comparator 301 may be configured to monitor the voltage directly, or calculate the voltage by integrating an electric current flowing through the diode or electrical contact over a period of time. The first voltage comparator 301 may be controllably activated or deactivated by the controller 310. The first voltage comparator 301 may be a continuous comparator. Namely, the first voltage comparator 301 may be configured to be activated continuously, and monitor the voltage continuously. The first voltage comparator 301 configured as a continuous comparator reduces the chance that the system 121 misses signals generated by an incident X-ray photon. The first voltage comparator 301 configured as a continuous comparator is especially suitable when the incident X-ray intensity is relatively high. The first voltage comparator 301 may be a clocked comparator, which has the benefit of lower power consumption. The first voltage comparator 301 configured as a clocked comparator may cause the system 121 to miss signals generated by some incident X-ray photons. When the incident X-ray intensity is low, the chance of missing an incident X-ray photon is low because the time interval between two successive photons is relatively long. Therefore, the first voltage comparator 301 configured as a clocked comparator is especially suitable when the incident X-ray intensity is relatively low. The first threshold may be 1-5%, 5-10%, 10%-20%, 20-30%, 30-40% or 40-50% of the maximum voltage one incident X-ray photon may generate on the electric contact 119B. The maximum voltage may depend on the energy of the incident X-ray photon (i.e., the wavelength of the incident X-ray), the material of the X-ray absorption layer 110, and other factors. For example, the first threshold may be 50 mV, 100 mV, 150 mV, or 200 mV.

The second voltage comparator 302 is configured to compare the voltage to a second threshold. The second voltage comparator 302 may be configured to monitor the voltage directly, or calculate the voltage by integrating an electric current flowing through the diode or the electrical contact over a period of time. The second voltage comparator 302 may be a continuous comparator. The second voltage comparator 302 may be controllably activate or deactivated by the controller 310. When the second voltage comparator 302 is deactivated, the power consumption of the second voltage comparator 302 may be less than 1%, less than 5%, less than 10% or less than 20% of the power consumption when the second voltage comparator 302 is activated. The absolute value of the second threshold is greater than the absolute value of the first threshold. As used herein, the term "absolute value" or "modulus" |x| of a real number x is the non-negative value of x without regard to its sign. Namely, $$|x| = \begin{cases} x, & \text{if } x \geq 0 \\ -x, & \text{if } x \leq 0 \end{cases}.$$

The second threshold may be 200%-300% of the first threshold. For example, the second threshold may be 100 mV, 150 mV, 200 mV, 250 mV or 300 mV. The second voltage comparator 302 and the first voltage comparator 310 may be the same component. Namely, the system 121 may have one voltage comparator that can compare a voltage with two different thresholds at different times.

The first voltage comparator 301 or the second voltage comparator 302 may include one or more op-amps or any other suitable circuitry. The first voltage comparator 301 or the second voltage comparator 302 may have a high speed to allow the system 121 to operate under a high flux of incident X-ray. However, having a high speed is often at the cost of power consumption.

The counters 320 may be a software component (e.g., numbers stored in a computer memory) or a hardware component (e.g., 4017 IC and 7490 IC). Each counter 320 is associated with a bin for an energy range. For example, counter 320A may be associated with a bin for 70-71 KeV, counter 320B may be associated with a bin for 71-72 KeV, counter 320C may be associated with a bin for 72-73 KeV, counter 320D may be associated with a bin for 73-74 KeV. When the energy of an incident X-ray photons is determined by the ADC 306 to be in the bin a counter 320 is associated with, the number registered in the counter 320 is increased by one.

The controller 310 may be a hardware component such as a microcontroller and a microprocessor. The controller 310 is configured to start a time delay from a time at which the first voltage comparator 301 determines that the absolute value of the voltage equals or exceeds the absolute value of the first threshold (e.g., the absolute value of the voltage increases from below the absolute value of the first threshold to a value equal to or above the absolute value of the first threshold). The absolute value is used here because the voltage may be negative or positive, depending on whether the voltage of the cathode or the anode of the diode or which electrical contact is used. The controller 310 may be configured to keep deactivated the second voltage comparator 302, the counter 320 and any other circuits the operation of the first voltage comparator 301 does not require, before the time at which the first voltage comparator 301 determines that the absolute value of the voltage equals or exceeds the absolute value of the first threshold. The time delay may expire after the voltage becomes stable, i.e., the rate of change of the voltage is substantially zero. The phase "the rate of change is substantially zero" means that temporal change is less than 0.1%/ns. The phase "the rate of change is substantially non-zero" means that temporal change of the voltage is at least 0.1%/ns.

The controller 310 may be configured to activate the second voltage comparator during (including the beginning and the expiration) the time delay. In an embodiment, the controller 310 is configured to activate the second voltage comparator at the beginning of the time delay. The term "activate" means causing the component to enter an operational state (e.g., by sending a signal such as a voltage pulse or a logic level, by providing power, etc.). The term "deactivate" means causing the component to enter a non-operational state (e.g., by sending a signal such as a voltage pulse or a logic level, by cut off power, etc.). The operational state may have higher power consumption (e.g., 10 times higher, 100 times higher, 1000 times higher) than the non-operational state. The controller 310 itself may be deactivated until the output of the first voltage comparator 301 activates the controller 310 when the absolute value of the voltage equals or exceeds the absolute value of the first threshold.

The controller 310 may be configured to cause the number registered by one of the counters 320 to increase by one, if, during the time delay, the second voltage comparator 302 determines that the absolute value of the voltage equals or exceeds the absolute value of the second threshold, and the energy of the X-ray photon falls in the bin associated with the counter 320.

The controller 310 may be configured to cause the ADC 306 to digitize the voltage upon expiration of the time delay and determine based on the voltage which bin the energy of the X-ray photon falls in.

The controller 310 may be configured to connect the electric contact 119B to an electrical ground, so as to reset the voltage and discharge any charge carriers accumulated on the electric contact 119B. In an embodiment, the electric contact 119B is connected to an electrical ground after the expiration of the time delay. In an embodiment, the electric contact 119B is connected to an electrical ground for a finite reset time period. The controller 310 may connect the electric contact 119B to the electrical ground by controlling the switch 305. The switch may be a transistor such as a field-effect transistor (FET).

In an embodiment, the system 121 has no analog filter network (e.g., a RC network). In an embodiment, the system 121 has no analog circuitry.

The ADC 306 may feed the voltage it measures to the controller 310 as an analog or digital signal. The ADC may be a successive-approximation-register (SAR) ADC (also called successive approximation ADC). An SAR ADC digitizes an analog signal via a binary search through all possible quantization levels before finally converging upon a digital output for the analog signal. An SAR ADC may have four main subcircuits: a sample and hold circuit to acquire the input voltage ($V_{in}$), an internal digital-analog converter (DAC) configured to supply an analog voltage comparator with an analog voltage equal to the digital code output of the successive approximation register (SAR), the analog voltage comparator that compares $V_{in}$ to the output of the internal DAC and outputs the result of the comparison to the SAR, the SAR configured to supply an approximate digital code of $V_{in}$ to the internal DAC. The SAR may be initialized so that the most significant bit (MSB) is equal to a digital 1. This code is fed into the internal DAC, which then supplies the analog equivalent of this digital code ($V_{ref}/2$) into the comparator for comparison with $V_{in}$. If this analog voltage exceeds $V_{in}$ the comparator causes the SAR to reset this bit; otherwise, the bit is left a 1. Then the next bit of the SAR is set to 1 and the same test is done, continuing this binary search until every bit in the SAR has been tested. The resulting code is the digital approximation of $V_{in}$ and is finally output by the SAR at the end of the digitization.

Figure 6:
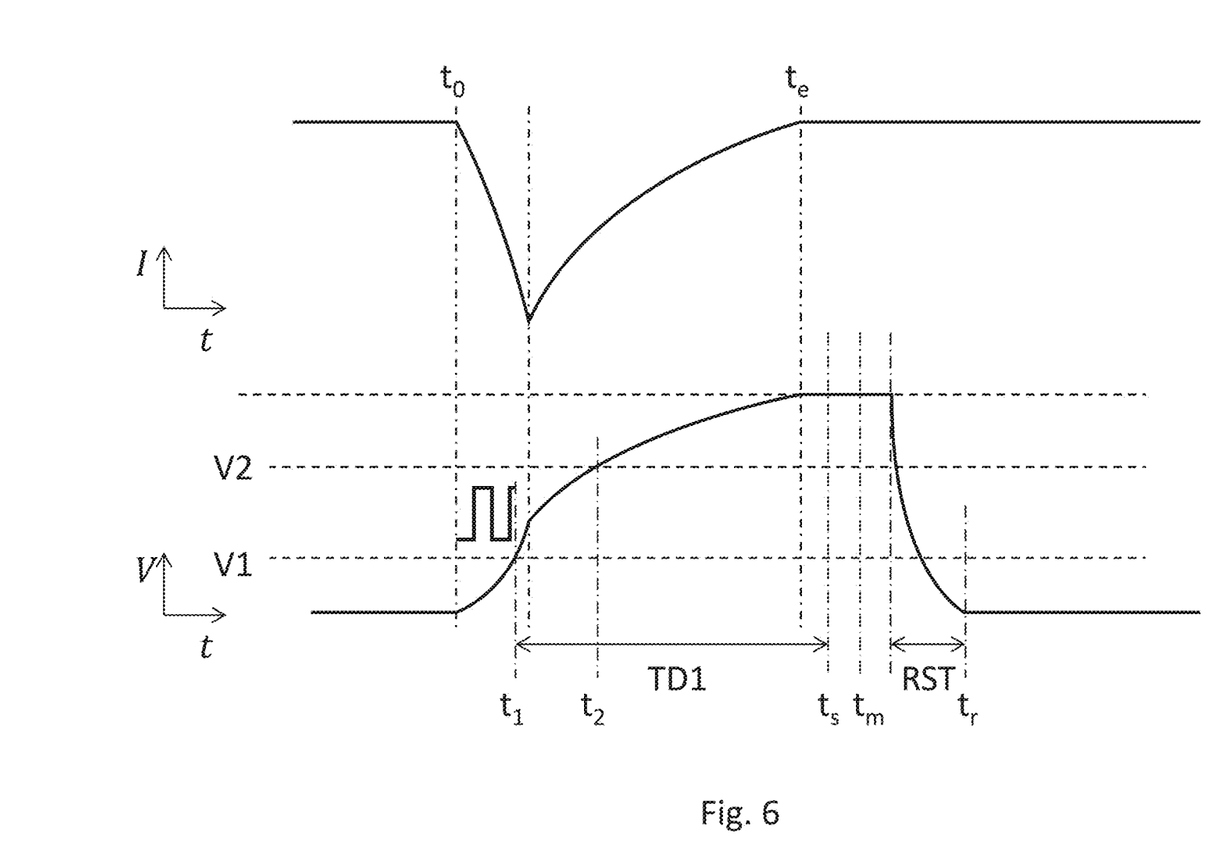
FIG. 6 schematically shows a temporal change of the electric current flowing through an electric contact (upper curve) caused by charge carriers generated by an X-ray photon incident on a pixel associated with the electric contact, and a corresponding temporal change of the voltage of the electric contact (lower curve).

The system 121 may include a capacitor module 309 electrically connected to the electric contact 119B, wherein the capacitor module is configured to collect charge carriers from the electric contact 119B. The capacitor module can include a capacitor in the feedback path of an amplifier. The amplifier configured as such is called a capacitive transimpedance amplifier (CTIA). CTIA has high dynamic range by keeping the amplifier from saturating and improves the signal-to-noise ratio by limiting the bandwidth in the signal path. Charge carriers from the electrode accumulate on the capacitor over a period of time ("integration period") (e.g., as shown in FIG. 6, between $t_s$ to $t_0$). After the integration period has expired, the capacitor voltage is sampled by the ADC 306 and then reset by a reset switch. The capacitor module 309 can include a capacitor directly connected to the electric contact 119B.

FIG. 6 schematically shows a temporal change of the electric current flowing through the electric contact 119B (upper curve) caused by charge carriers generated by an X-ray photon incident on the pixel 150 associated with the electric contact 119B, and a corresponding temporal change of the voltage of the electric contact 119B (lower curve). The voltage may be an integral of the electric current with respect to time. At time $t_0$, the X-ray photon hits the diode or the resistor, charge carriers start being generated in the pixel 150, electric current starts to flow through the electric contact 119B, and the absolute value of the voltage of the electric contact 119B starts to increase. At time $t_1$, the first voltage comparator 301 determines that the absolute value of the voltage equals or exceeds the absolute value of the first threshold V1, and the controller 310 starts the time delay TD1 and the controller 310 may deactivate the first voltage comparator 301 at the beginning of TD1. If the controller 310 is deactivated before $t_1$, the controller 310 is activated at $t_1$. During TD1, the controller 310 activates the second voltage comparator 302. The term "during" a time delay as used here means the beginning and the expiration (i.e., the end) and any time in between. For example, the controller 310 may activate the second voltage comparator 302 at the expiration of TD1. If during TD1, the second voltage comparator 302 determines that the absolute value of the voltage equals or exceeds the absolute value of the second threshold at time $t_2$, the controller 310 waits for stabilization of the voltage to stabilize. The voltage stabilizes at time $t_e$, when all charge carriers generated by the X-ray photon drift out of the X-ray absorption layer 110. At time $t_s$, the time delay TD1 expires. At or after time $t_e$, the controller 310 causes the ADC 306 to digitize the voltage and determines which bin the energy of the X-ray photons falls in. The controller 310 then causes the number registered by the counter 320 corresponding to the bin to increase by one. In the example of FIG. 6, time $t_s$ is after time $t_e$; namely TD1 expires after all charge carriers generated by the X-ray photon drift out of the X-ray absorption layer 110. If time $t_e$ cannot be easily measured, TD1 can be empirically chosen to allow sufficient time to collect essentially all charge carriers generated by an X-ray photon but not too long to risk have another incident X-ray photon. Namely, TD1 can be empirically chosen so that time $t_s$ is empirically after time $t_e$. Time $t_s$ is not necessarily after time $t_e$ because the controller 310 may disregard TD1 once V2 is reached and wait for time $t_e$. The rate of change of the difference between the voltage and the contribution to the voltage by the dark current is thus substantially zero at $t_e$. The controller 310 may be configured to deactivate the second voltage comparator 302 at expiration of TD1 or at $t_2$, or any time in between.

The voltage at time $t_e$ is proportional to the amount of charge carriers generated by the X-ray photon, which relates to the energy of the X-ray photon. The controller 310 may be configured to determine the bin the energy of the X-ray photon falls in, based on the output of the ADC 306.

After TD1 expires or digitization by the ADC 306, whichever later, the controller 310 connects the electric contact 119B to an electric ground for a reset period RST to allow charge carriers accumulated on the electric contact 119B to flow to the ground and reset the voltage. After RST, the system 121 is ready to detect another incident X-ray photon. Implicitly, the rate of incident X-ray photons the system 121 can handle in the example of FIG. 6 is limited by 1/(TD1+RST). If the first voltage comparator 301 has been deactivated, the controller 310 can activate it at any time before RST expires. If the controller 310 has been deactivated, it may be activated before RST expires.

Because the detector 100 has many pixels 150 that may operate in parallel, the detector can handle much higher rate of incident X-ray photons. This is because the rate of incidence on a particular pixel 150 is 1/N of the rate of incidence on the entire array of pixels, where N is the number of pixels.

Figure 7:
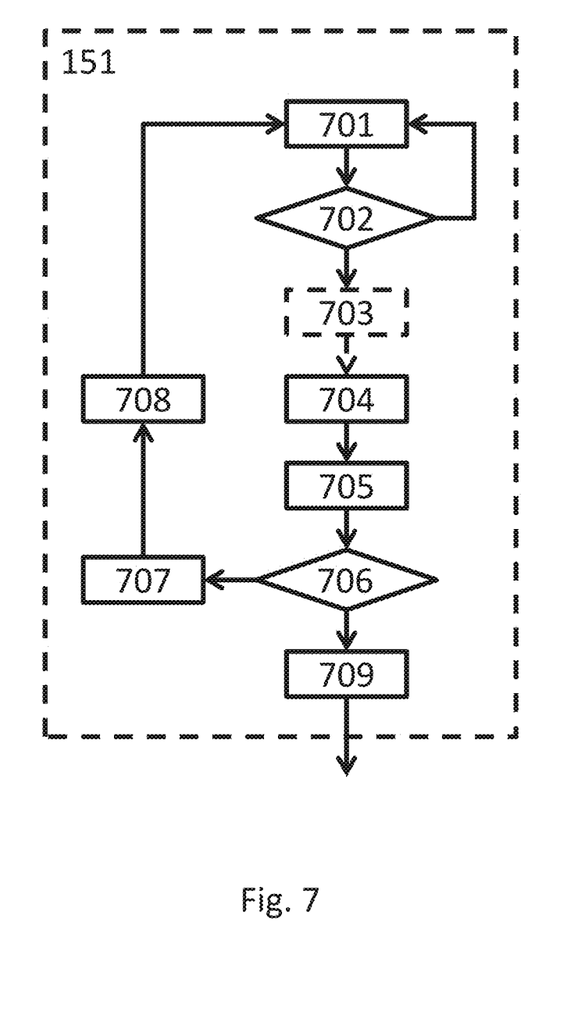
FIG. 7 shows an example flow chart for step 151 in FIG. 3, according to an embodiment.
Figure 8:
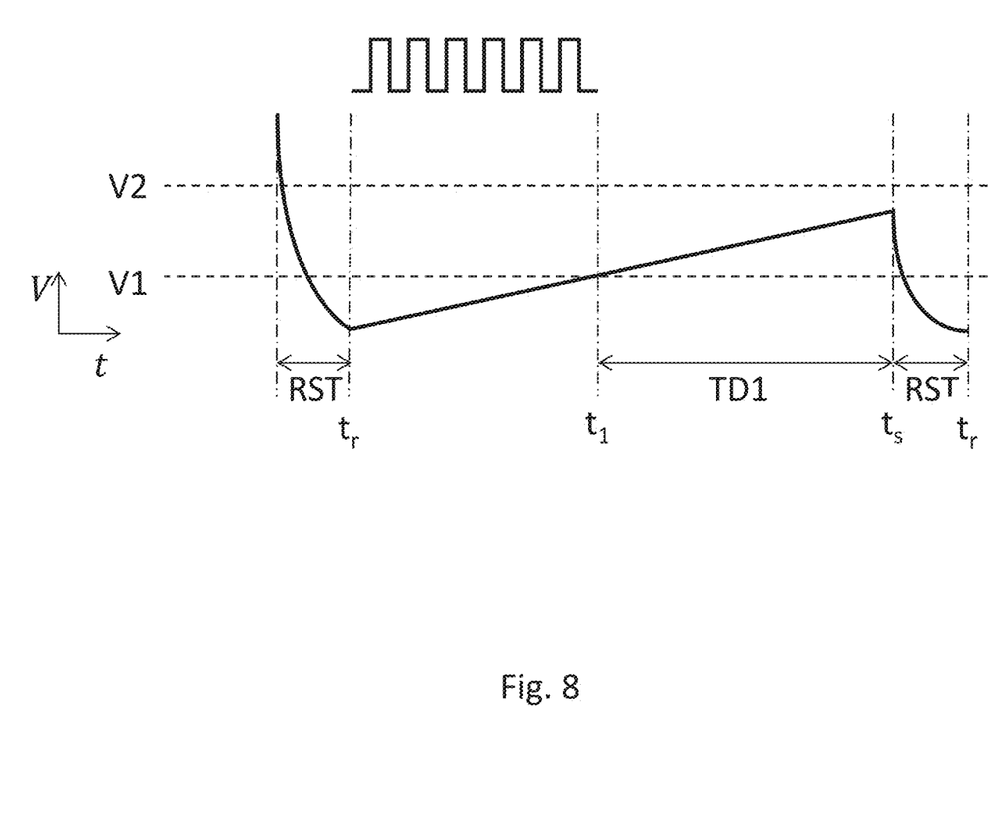
FIG. 8 schematically shows a temporal change of the voltage of the electric contact caused by the dark current, according to an embodiment.

FIG. 7 shows an example flow chart for step 151 in FIG. 3, according to an embodiment. In step 701, compare, e.g., using the first voltage comparator 301, a voltage of an electric contact 119B of a diode or a resistor exposed to X-ray photons (e.g., fluorescent X-ray), to the first threshold. In step 702, determine, e.g., with the controller 310, whether the absolute value of the voltage equals or exceeds the absolute value of the first threshold V1. If the absolute value of the voltage does not equal or exceed the absolute value of the first threshold, the method goes back to step 701. If the absolute value of the voltage equals or exceeds the absolute value of the first threshold, continue to step 703. In step 703, measure $T=(t_1-t_0)$. In step 704, start, e.g., using the controller 310, the time delay TD1. In step 705, compare, e.g., using the second voltage comparator 302, the voltage to the second threshold. In step 706, determine, e.g., using the controller 310, whether the absolute value of the voltage equals or exceeds the absolute value of the second threshold V2. If the absolute value of the voltage does not equal or exceed the absolute value of the second threshold, the method goes to step 707. In step 707, measure the contribution of the dark current to the voltage using T. In an example, determine whether T is greater than the largest T previously measured ($T_{max}$). $T_{max}=0$ if T is not previously measured. If T is greater than $T_{max}$, replace $T_{max}$ with T (i.e., T becomes the new $T_{max}$). The contribution of the dark current to the voltage is at a rate of $V1/T_{max}$. If the dark current is measured as in this example, the contribution of the dark current in step 709 is $((t_m-t_r)\cdot V1/T_{max})$, where $t_r$ is the end of the last reset period. $(t_m-t_r)$, like any time intervals in this disclosure, can be measured by counting pulses (e.g., counting clock cycles or clock pulses). $T_{max}$ may be reset to zero before each measurement with the detector 100. T may be measured by counting the number of pulses between $t_1$ and $t_0$, as schematically shown in FIG. 6 and FIG. 8. Another way to measure the contribution of the dark current to the voltage using T includes extracting a parameter of the distribution of T (e.g., the expected value of T ($T_{expected}$)) and estimate the rate of the contribution of the dark current to the voltage as $V1/T_{expected}$. In step 708, reset the voltage to an electrical ground, e.g., by connecting the electric contact 119B to an electrical ground. If the absolute value of the voltage equals or exceeds the absolute value of the second threshold, continue to step 709. In step 709, measure the voltage after it stabilizes, at time $t_m$, and subtract an contribution from a dark current to the measured voltage. Time $t_m$ can be any time after TD1 expires and before RST. The result is provided to ADC in step 152 in FIG. 3 The time when the reset period ends (e.g., the time when the electric contact 119B is disconnected from the electrical ground) is $t_r$.

FIG. 8 schematically shows a temporal change of the voltage of the electric contact 119B caused by the dark current, according to an embodiment. After RST, the voltage increase due to the dark current. The higher the dark current, the less time it takes for the voltage to reach V1 (namely shorter T). Therefore, T is a measure of the dark current. The dark current is unlikely large enough to cause the voltage to reach V2 during TD1 but current caused by an incident X-ray photon is probably large enough to do so. This difference may be used to identify the effect of the dark current. The flow in FIG. 8 may be carried out in each pixel 150 as the pixel 150 measures a series of incident X-ray photons, which will allow capturing the changes of the dark current (e.g., caused by changing environment such as temperature).

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A detector, comprising:
    a plurality of pixels, each pixel configured to count numbers of X-ray photons incident thereon whose energy falls in a plurality of bins of different energy ranges respectively, within a period of time; and
    wherein the detector is configured to sum the numbers counted by all the pixels from only the bins of the same energy range.

2. The detector of claim 1, further configured to compile the added numbers as a spectrum of the X-ray photons incident on the detector.

3. The detector of claim 1, wherein the plurality of pixels are arranged in an array.

4. The detector of claim 1, wherein the pixels are configured to count the numbers of X-ray photons within a same period of time.

5. The detector of claim 1, wherein each of the pixels comprises an analog-to-digital converter (ADC) configured to digitize an analog signal representing the energy of an incident X-ray photon into a digital signal.

6. The detector of claim 5, wherein the ADC is a successive-approximation-register (SAR) ADC.

7. The detector of claim 1, wherein the pixels are configured to operate in parallel.

8. The detector of claim 1, wherein each of the pixels is configured to measure its dark current.

9. The detector of claim 8, wherein each of the pixels is configured to measure its dark current before or concurrently with each X-ray photon incident thereon.

10. The detector of claim 8, wherein each of the pixels is configured to deduct a contribution of the dark current from the energy of an X-ray photon incident thereon.

11. The detector of claim 8, wherein each of the pixels is configured to measure its dark current by measuring a time it takes for a voltage to increase by a threshold.

12. The detector of claim 1, further comprising:
    an X-ray absorption layer comprising an electric contact;
    a first voltage comparator configured to compare a voltage of the electric contact to a first threshold;
    a second voltage comparator configured to compare the voltage to a second threshold;
    a controller;
    a plurality of counters each associated with a bin and configured to register a number of X-ray photons absorbed by one of the pixels wherein the energy of the X-ray photons falls in the bin;
    wherein the controller is configured to start a time delay from a time at which the first voltage comparator determines that an absolute value of the voltage equals or exceeds an absolute value of the first threshold;
    wherein the controller is configured to determine whether an energy of an X-ray photon falls into the bin;
    wherein the controller is configured to cause the number registered by the counter associated with the bin to increase by one.

13. The detector of claim 12, further comprising a capacitor module electrically connected to the electric contact, wherein the capacitor module is configured to collect charge carriers from the electric contact.

14. The detector of claim 12, wherein the controller is configured to activate the second voltage comparator at a beginning or expiration of the time delay.

15. The detector of claim 12, wherein the controller is configured to connect the electric contact to an electrical ground.

16. The detector of claim 12, wherein a rate of change of the voltage is substantially zero at expiration of the time delay.

17. The detector of claim 12, wherein the X-ray absorption layer comprises a diode.

18. The detector of claim 12, wherein the X-ray absorption layer comprises silicon, germanium, GaAs, CdTe, CdZnTe, or a combination thereof.

19. The detector of claim 1, wherein the apparatus does not comprise a scintillator.

20. A method for measuring an energy spectrum of X-ray, comprising:
    exposing a detector with a plurality of pixels to X-ray;
    determining a number of X-ray photons for each of the pixels for one bin of a plurality of bins of different energy ranges respectively, wherein energy of the X-ray photon falls in the one bin;
    summing the numbers determined for all the pixels from only the bins of the same energy range.

21. The method of claim 20, wherein determining the number comprises subtracting a contribution of dark current in the each pixel.

22. The method of claim 20, wherein determining the number comprises analog-to-digital conversion.

* * * * *